(12) United States Patent
King

(10) Patent No.: US 6,711,755 B2
(45) Date of Patent: Mar. 30, 2004

(54) PROSTHETIC DEVICE HAVING A POLYARYLETHERKETONE COMPONENT WITH ENHANCED WETTABILITY AND A METHOD FOR MAKING THE SAME

(75) Inventor: Richard King, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 98 days.

(21) Appl. No.: 10/108,852

(22) Filed: Mar. 28, 2002

(65) Prior Publication Data

US 2003/0195327 A1 Oct. 16, 2003

(51) Int. Cl.[7] .............................. A61F 1/24; A61F 1/00
(52) U.S. Cl. ............................... 528/1.9; 3/1; 528/220; 528/487; 528/499; 623/16
(58) Field of Search ............................... 528/220, 487, 528/499; 623/16; 3/1.9, 1

(56) References Cited

U.S. PATENT DOCUMENTS

| | | |
|---|---|---|
| 4,181,983 A | 1/1980 | Kulkarni |
| 4,206,516 A | 6/1980 | Pilliar |
| 4,227,265 A | 10/1980 | Frey |
| 4,281,420 A | 8/1981 | Raab |
| 4,320,224 A | 3/1982 | Rose et al. |
| 4,662,887 A | 5/1987 | Turner et al. |
| 5,443,512 A | 8/1995 | Parr et al. |
| 5,480,449 A | 1/1996 | Hamilton et al. |
| 5,591,233 A | 1/1997 | Kelman et al. |

FOREIGN PATENT DOCUMENTS

| | | |
|---|---|---|
| EP | 0 171 884 B1 | 12/1992 |
| WO | WO 02/00270 A1 | 1/2002 |
| WO | WO 02/00271 A1 | 1/2002 |

OTHER PUBLICATIONS

"Ultrapek High–heat–resistant Poly(arylether ketone) (PEAK) Product line Properties Processing" BASF publication (pp. 1–44) Undated.

"Ultrapek High temperature resistant poly(arylehter ketone) (PEAK) Range Chart Features Applications Typical Values" BASF publication (10 ppages) Undated.

Victrex PEEK "Material Properties Guide" publication (pp. 1–47) Undated.

Olivier Noiset et al., XP–001033579, "*Fibronectin adsorption or/and covalent grafting on chemically modified PEEK film surfaces*", J. Biomater, Sci. Polymer Edn. vol. 10, No. 6, pp. 657–677 (1999).

Catherine Henneuse et al., "*Surface carboxylation of PEEK film by selective wet–chemistry*", Polymer vol. 39, No. 4, pp. 835–844 (1998).

European Search Report for European Application No. 03251926.6–1219–, dated Aug. 13, 2003.

*Primary Examiner*—Duc Truong
(74) *Attorney, Agent, or Firm*—Barnes & Thornburg

(57) ABSTRACT

A prosthetic device having a polyaryletherketone component with a wettable surface is disclosed. The surface of the polyaryletherketone component has a surface chemistry which enhances the ability of tissues to grow directly thereon. An associated method for enhancing the wettability of a prosthetic device is also disclosed.

5 Claims, 3 Drawing Sheets

US 6,711,755 B2

PROSTHETIC DEVICE HAVING A POLYARYLETHERKETONE COMPONENT WITH ENHANCED WETTABILITY AND A METHOD FOR MAKING THE SAME

TECHNICAL FIELD OF THE DISCLOSURE

The present disclosure relates generally to prosthetic devices, and more particularly to prosthetic devices having a polyaryletherketone component with enhanced wettability.

BACKGROUND

Materials used to fabricate prosthetic devices, such as an orthopedic implant, need to possess certain mechanical and chemical properties in order to function and exist in contact with the biological tissue of a living organism. For example, these materials should possess the appropriate mechanical/chemical properties so they do not induce undesirable reactions in the body such as blood clotting, tissue death, tumor formation, allergic reaction, foreign body reaction (rejection), and/or inflammatory reaction. In addition, the materials used to fabricate prosthetic devices should posses the appropriate strength, elasticity, permeability, and flexibility in order for the prosthetic device to function properly for its intended purpose. Moreover, it is desirable that these materials (i) sterilize easily and (ii) substantially maintain their physical properties during the time the prosthetic device remains in contact with the biological tissue.

There are a number of materials currently available which possess one or more of the above described characteristics. Accordingly, these materials can be utilized for fabricating prosthetic devices. However, a drawback to some of these materials is that they do not present a surface which is well suited for direct tissue growth (e.g. bone) onto or into the prosthetic device. As such, prosthetic devices fabricated from these materials have a decreased ability to form a suitably stable mechanical unit with the neighboring tissues (e.g. bone). Therefore, these prosthetic devices can become loose or unstable relative to the neighboring tissue which can result in the device functioning less efficiently or not functioning at all. A loose or unstable prosthetic device can also induce an excessive tissue response and cause the patient discomfort and pain. Finally, a loose prosthetic device is deemed to have failed, and thus has to be surgically removed which further burdens the patient.

Accordingly, in light of the above discussion, a material for fabricating a prosthetic device which addresses the above described drawback is needed.

SUMMARY

In accordance with one exemplary embodiment, there is provided a prosthetic device. The prosthetic device includes a polyaryletherketone component. The polyaryletherketone component has a surface, and the surface has an tissuegenically effective amount of sulfonation thereon.

In accordance with another exemplary embodiment, there is provided a prosthetic arrangement for implanting in the body of a patient. The prosthetic arrangement includes an orthopedic implant device having a polyaryletherketone component. The polyaryletherketone component has a surface, and the surface has an tissuegenically effective amount of sulfonation thereon.

In accordance with yet another exemplary embodiment, there is provided an orthopedic device. The orthopedic device includes a polyaryletherketone component. The polyaryletherketone component has a surface, and the surface has an tissuegenically effective amount of sulfonation thereon.

In accordance with still another exemplary embodiment, there is provided a method of preparing a prosthetic device having a polyaryletherketone component. The method includes (a) contacting a surface of the polyaryletherketone component of the prosthetic device with a sulfonation agent and (b) sulfonating the surface of the polyarlyetherketone component.

In accordance with yet another exemplary embodiment, there is provided a prosthetic device having a polyaryletherketone component prepared by subjecting the polyaryletherketone component to a sulfonation reaction.

In accordance with still another exemplary embodiment, there is provided a method of preparing a prosthetic device which includes a polyaryletherketone component having a surface. The method includes reacting the surface of the polyaryletherketone component of the prosthetic device with a chemical so that the wettability of the surface is increased.

In accordance with yet another exemplary embodiment, there is provided a prosthetic device. The prosthetic device includes a polyaryletherketone component. The polyaryletherketone component has a surface which has a wettability such that a contact angle of a bead of water positioned on the surface has a value less than 78°.

In accordance with still another exemplary embodiment, there is provided a prosthetic device. The prosthetic device includes an orthopedic implant having a polyaryletherketone component. The polyaryletherketone component has a surface which has a wettability such that a contact angle of a bead of water positioned on the surface has a value less than 78°.

In accordance with yet another exemplary embodiment, there is provided a polyaryletherketone component. The polyaryletherketone component includes a surface having a wettability such that a contact angle of a bead of water positioned on the surface has a value less than 78°.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DISCLOSURE

Figure 1:
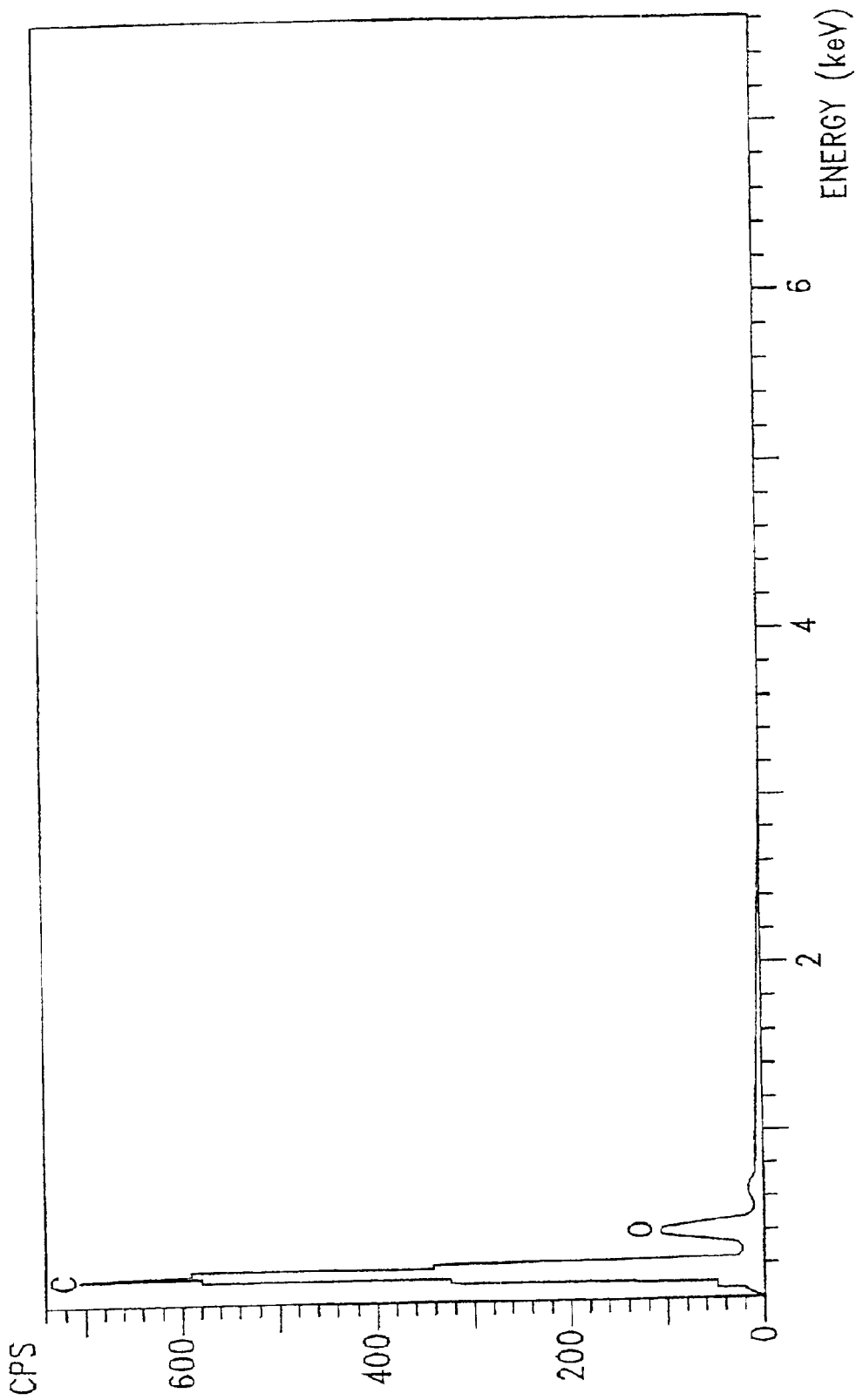
FIG. 1 depicts an Energy-Dispersive X-Ray Analysis spectrum of a polyaryletherketone sample prior to being subjected to a sulfonation reaction.

The present invention relates to prosthetic devices having enhanced wettability and methods of making the same. The prosthetic devices described herein can be utilized as endoprosthetic devices configured to be implanted within the body of a patient. In particular, the prosthetic devices described herein can be utilized as orthopedic devices, such as an orthopedic implant of any type, condition, shape, or configuration. For example, these orthopedic implants may be utilized in a number of joint replacement or repair procedures such as surgical procedures associated with the hip, shoulders, knees, ankles, knuckles, or any other joint.

It should be appreciated that the prosthetic devices described herein include a polyaryletherketone component. It should also be appreciated that only a portion of the prosthetic device can be made from the polyaryletherketone component, or the entire prosthetic device can be made from the polyaryletherketone component. What is meant herein by a polyaryletherketone component is that the component includes one or more polymers from the polyaryletherketone family, including, but not limited to, a polyaryletherketone which contains repeating units of the following general formula:

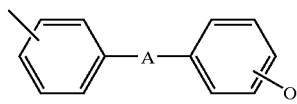

where A is a direct link, a sulfur atom, a divalent hydrocarbon radical or a group —Q—(Ar—Q$^1$)$_n$ in which Q is —CO—, —SO$_2$—, or —O—, Q$^1$ is —O—, and Ar is a divalent aromatic radical and n is 0, 1, 2 or 3. In particular, the polyaryletherketone can contain repeating units of:

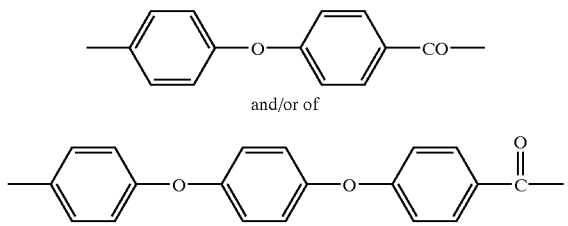

and/or of

Polyaryletherketones which can be utilized in the present invention are described in U.S. Pat. No. 4,320,224 which is incorporated herein by reference. In addition, polyaryletherketones which can be utilized in the present invention are commercially available from Victrex plc, located in Lancashire, England. For example, a polyaryetheretherketone (also known as PEEK™) having the oxy-1,4-phenylene-oxy-1,4-phenylene-carbonyl-1,4-phenylene repeat unit, which is shown again below, is commercially available from Victrex plc. in various grades (e.g. 450G, 381G, and 150G)

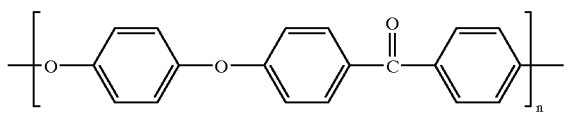

It should be appreciated that a prosthetic device of the present invention is subject to a chemical reaction which increases its "wettability". What is meant herein by "wettability" is the ability of a solid surface (e.g. the surface of the polyaryletherketone component) to be wetted when in contact with a liquid (e.g. water); that is the surface tension of the liquid is reduced so the liquid spreads over the surface. In particular, a surface of the polyaryletherketone component of the prosthetic device is reacted with a chemical so that the wettability of the surface is increased. (Note that, as used herein, the term "surface" includes the interior surface of pores or cavities defined in the prosthetic device. In particular the interior surface of pores or cavities defined in the polyaryletherketone component of the prosthetic device.) For example, the surface of the polyaryletherketone component of the prosthetic device can be reacted with a chemical so that the hydrophilicity of the surface is increased. What is meant herein by "hydrophilicity" is a measure of the affinity of the solid surface (e.g. the surface of the polyaryletherketone component) for attracting, adsorbing, or absorbing water.

The increase in the wettability of the surface of a polyaryletherketone component as a result of the aforementioned chemical reaction can be measured by any known appropriate technique. For example, one technique for measuring the increase in wettability of the surface of the polyaryletherketone component is to measure the contact angle θ of a bead of liquid (e.g. water) at the interface of the bead of liquid and the surface of the polyaryletherketone component. For example, the lower the contact angle θ of a bead of water at the interface of the bead of water and the surface of the polyaryletherketone component, the greater the wettability of the surface of the polyaryletherketone component. Preferably, the surface of the polyaryletherketone component of the prosthetic device is reacted with a chemical so that the contact angle of a bead of water at the interface of the bead of water and the surface of the polyaryletherketone component is less than 78°. For example, after increasing the wettability of the surface of the polyaryletherketone component, it is preferable that the aforementioned contact angle between the bead of water and the surface is within a range of about 77° to about 40°. For example, contact angles within a range of about 60° to about 40° are particularly desirable. However, it should also be appreciated that contact angles between a bead of water and a surface of a polyaryletherketone component which are less than about 40°, for example less than about 30°, are even more preferable as long as the wettability increasing process the surface of the polyaryletherketone component is subjected to satisfies the criteria discussed below.

Now turning to the above discussed chemical reaction, it should be appreciated that any appropriate reaction which chemically alters the surface of the polyaryletherketone component so as to increase its wettability can be utilized. However, it should also be appreciated that the chemical alteration of the surface of the polyaryletherketone component should not adversely affect, to any significant degree, its ability to be implanted in the body of a living organism, such as a human patient. In other words, after the chemical alteration the polyaryletherketone component should be "biocompatible". As used herein, the polyaryletherketone component is characterized as being "biocompatible" if it is capable of functioning or existing in contact with biological fluid and/or tissue of a living organism with a net beneficial affect on the living organism. In addition, the above described chemical alteration should not adversely affect, to any significant degree, the desirable chemical and/or mechanical properties of the polyaryletherketone component. For example, the chemical alteration should not erode the surface of the polyaryletherketone to any significant degree.

One method of increasing the wettability of the prosthetic device is to react the surface of the polyaryletherketone component with a chemical so that polar functional groups are disposed on the surface. The greater the number of polar groups disposed on the surface, the greater the wettability of the surface. These polar functional groups can be disposed on the surface via the formation of covalent bonds between the polar functional groups and chemical groups present on the surface of the polyaryletherketone component. However, any other appropriate chemical bonding mechanism (e.g. ionic) can be utilized to dispose the polar functional groups on the component surface as long as the bonding mechanism satisfies the aforementioned criteria of increasing the surface wettability while not adversely affecting, to any significant degree, the component's (i) ability to be implanted into a living body and/or (ii) its mechanical properties.

The above discussed wettability enhancing chemical reaction can be performed on the assembled prosthetic device or on the polyaryletherketone components prior to assembly into the prosthetic device. In addition, the wettability enhancing chemical reaction can be performed on polyaryletherketones in various physical states, including but not limited to, polyaryletherketone resins used to fabricate the polyaryletherketone component, polyaryletherketone composites used to fabricate the polyaryletherketone component, and porous polyaryletherketone structures used to fabricate the polyaryletherketone component.

An example of one chemical reaction which can be used to increase the wettability of the prosthetic device while satisfying the above discussed criteria is sulfonation. What is meant herein by sulfonation is the substitution of —$SO_3H$ groups from a sulfonation agent for hydrogen atoms. For example, the sulfonation of the surface of a polyaryletherketone component which includes the repeating unit

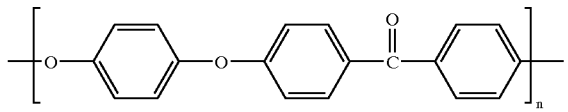

can be illustrated by the following equation:

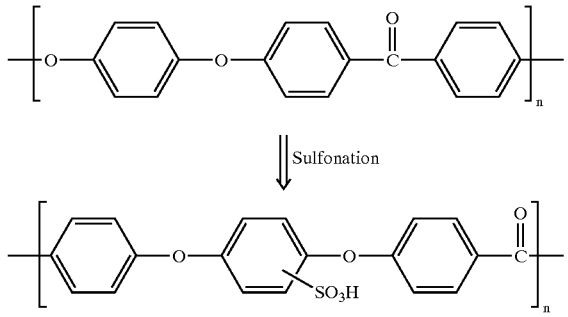

and salts thereof. Examples of sulfonation agents which can be utilized in the above illustrated equation include, but are not limited to, sulfuric acid (>95%), fuming sulfuric acid, and sulfur trioxide.

The sulfonation of a surface of a polyaryletherketone component can be accomplished by contacting the surface with a sulfonation agent at about room temperature up to a temperature of about 80° C. for a time period between about 5 minutes up to about 20 minutes. The particular sulfonation reaction conditions (e.g. temperature, time period, concentration of the sulfonation agent) utilized will depend upon the specific polyaryletherketone surface being sulfonated, the particular sulfonation agent selected, and the degree of sulfonation desired. For example, some members of the polyaryletherketone family will require more vigorous sulfonation conditions to achieve the desired degree of sulfonation, while other members will require less vigorous sulfonation conditions, depending upon, for example, the chemical nature of the polyaryletherketone component.

An example, of a sulfonation reaction is described below. Samples of Victrex 450G PEEK™ films (0.004 inch) were cleaned with isopropyl alcohol and vacuum dried at 60° C. prior to being subjected to the sulfonation reaction. Thereafter each PEEK™ film sample was placed in contact with 96.5% sulfuric acid at room temperature. Each PEEK™ film was kept in contact with the sulfuric acid for a time period of at least 10 minutes. At this point (i.e. 10 minutes) some of the PEEK™ film samples were removed from the sulfuric acid and thoroughly washed with water. After the aqueous wash, the PEEK™ film samples were neutralized with a 0.5N potassium hydroxide solution, a saturated calcium hydroxide solution, or a 0.25 sodium citrate solution. The neutralized PEEK™ film samples were then rinsed with water and vacuum dried at 60° C. prior to surface characterization. The remaining PEEK™ film samples were kept in contact with the sulfuric acid for various times up to about 20 minutes. When these PEEK™ film samples were removed from the sulfuric acid they were neutralized and dried in the same manner as described above prior to surface characterization.

Figure 2:
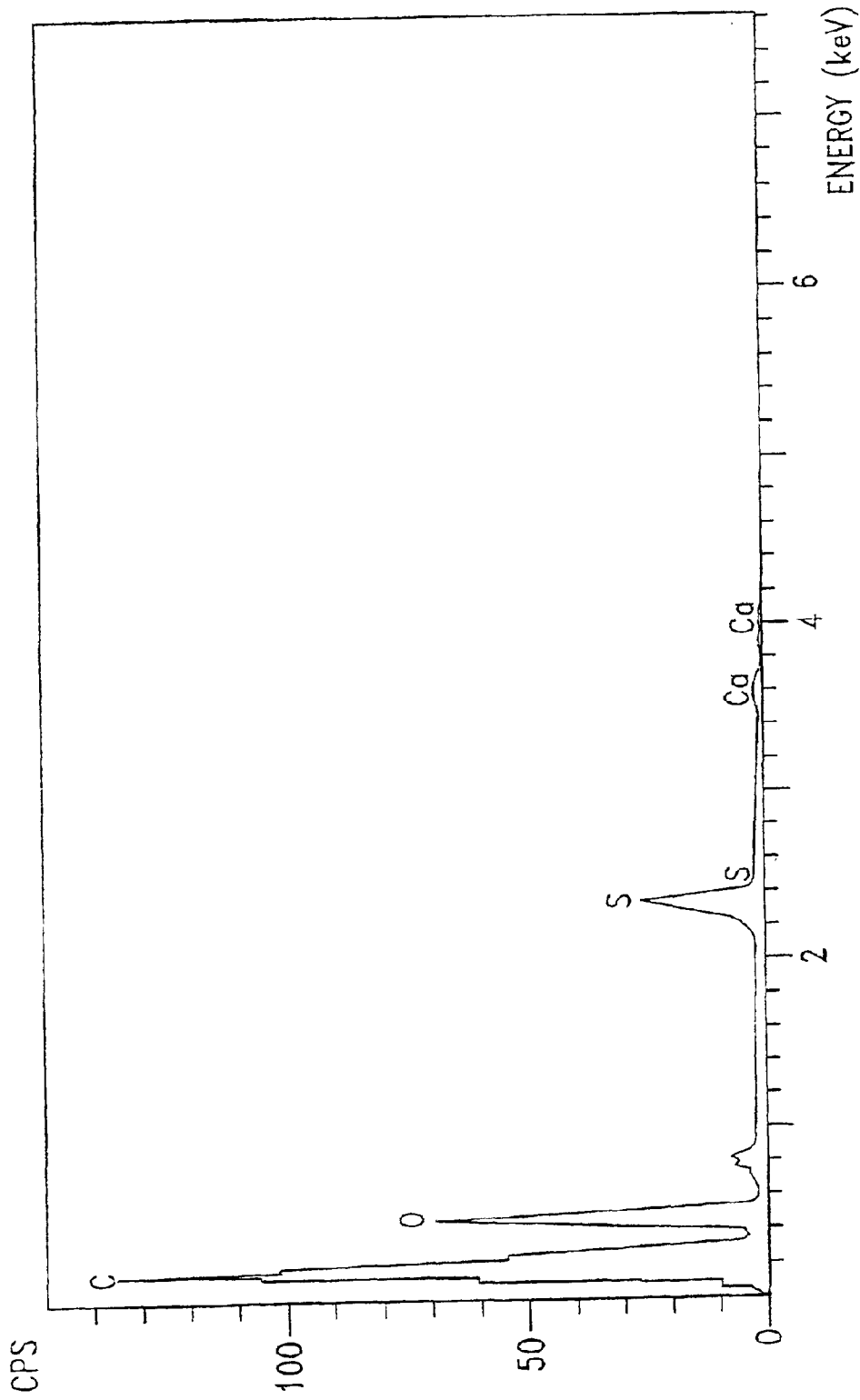
FIG. 2 depicts an Energy-Dispersive X-Ray Analysis spectrum of a polyaryletherketone sample after being subjected to a sulfonation reaction neutralized with calcium hydroxide.
Figure 3:
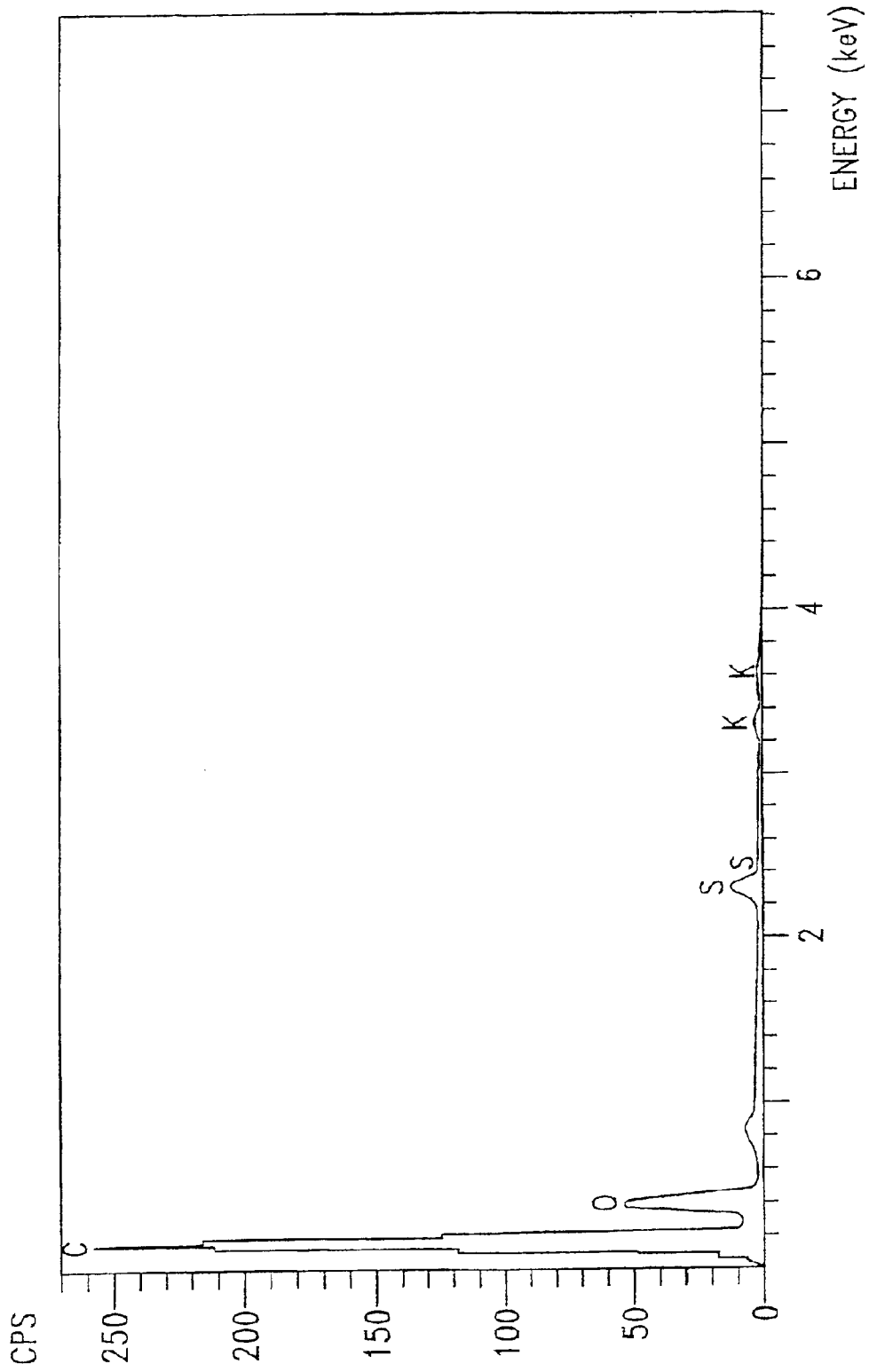
FIG. 3 depicts an Energy-Dispersive X-Ray Analysis spectrum of a polyaryletherketone sample after being subjected to a sulfonation reaction neutralized with potassium hydroxide.

The Energy-Dispersive X-Ray Analysis (EDXA) was utilized for surface characterization of the PEEK™ samples. In particular, the EDXA spectrum of the above described PEEK™ films were taken before and after being subjected to the sulfonation reaction. In particular, FIG. 1 illustrates the EDXA spectrum of a PEEK™ film prior to being subjected to the sulfonation reaction. As shown in the spectrum of FIG. 1, carbon and oxygen are detected by the EDXA analysis which is consistent with the surface characteristics of a PEEK™ sample prior to sulfonation. With respect to FIG. 2, it illustrates the EDXA spectrum of a PEEK™ film after being subjected to the sulfonation reaction and then neutralized with a calcium hydroxide solution. As shown in the spectrum of FIG. 2, the EDXA analysis detects carbon, oxygen, sulfur, and calcium which is consistent with the expected surface characteristics of a PEEK™ sample after being subjected to sulfonation and then neutralized with a calcium hydroxide solution. FIG. 3 illustrates the EDXA spectrum of a PEEK™ film after being subjected to the sulfonation reaction and then neutralized with a potassium hydroxide solution. As shown in the spectrum of FIG. 3, the EDXA analysis detects carbon, oxygen, sulfur, and potassium which is consistent with the expected surface characteristics of a PEEK™ sample after being subjected to sulfonation and then neutralized with a potassium hydroxide solution.

With respect to the surface wettability of PEEK™ sulfonated in the above described manner, contact angles of about 51° with respect to a bead of water were obtained with these samples. This is in contrast to an unsulfonated PEEK™ sample which has a contact angle of 78° or more with respect to a bead of water. Accordingly, the above described sulfonation reaction increased the surface wettability of these PEEK™ samples.

It should be understood that enhancing the wettability of a surface of a prosthetic device results in the surface becoming "tissuegenic". What is meant herein by a "tissuegenic" surface is that the surface has a capacity, or an increased capacity, for tissue to grow directly onto or into the surface. In other words, tissues have a greater affinity for a tissuegenic surface. Tissues which can grow directly onto or into a tissuegenic surface include, but are not limited to, bone, cartilage, and tendon.

As discussed above, one way of enhancing the wettability of a surface, and thereby rendering the surface "tissuegenic", is to dispose a sufficient amount of polar functional groups on the surface via a chemical reaction. Accordingly, a surface of a polyaryletherketone component having an tissuegenically effective amount of polar functional groups disposed thereon will have a capacity, or an increased capacity, for tissue, such as bone, to grow directly onto or into the surface. For example, a polyaryletherketone component surface having an tissuegenically effective amount of sulfonation thereon (i.e. an effective amount of —$SO_3H$ groups and salts thereof disposed thereon) has a capacity, or an increased capacity as compared to the surface prior to the sulfonation, for tissue (e.g. bone) to grow directly onto or into the surface.

The tissuegenicity, or the increase in the tissuegenicity, of a surface of a polyaryletherketone component as a result of the aforementioned chemical reaction can be measured by any known appropriate technique. For example, one technique for measuring the tissuegenicity, or the increase in tissuegenicity, of the surface of the polyaryletherketone component is to measure the shear strength or tensile strength of the interface between the surface of the polyaryletherketone component and the contacting tissue (e.g. bone). The greater the shear strength or tensile strength of the interface between the surface of the polyaryletherketone component and the contacting tissue the greater the surface tissuegenicity. Accordingly, a prosthetic device having a polyaryletherketone component with a tissuegenic surface has an enhanced capacity to form a suitably stable mechanical unit with the neighboring tissues (e.g. bone). Therefore, these prosthetic devices have a decreased probability of becoming loose or unstable relative to the neighboring tissue and thereby functioning less efficiently or not functioning at all.

While the disclosure is susceptible to various modifications and alternative forms, specific exemplary embodiments thereof have been shown by way of example in the drawings and has herein been described in detail. It should be understood, however, that there is no intent to limit the disclosure to the particular forms disclosed, but on the contrary, the intention is to cover all modifications, equivalents, and alternatives falling within the spirit and scope of the disclosure.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

What is claimed is:

1. A prosthetic device, comprising:

a polyaryletherketone component, wherein (i) said polyaryletherketone component has a surface and (ii) said surface has a wettability such that a contact angle of a bead of water positioned on said surface has a value less than 78°.

2. The prosthetic device of claim 1, wherein:

said contact angle is about 51°.

3. A prosthetic device, comprising:

an orthopedic implant having a polyaryletherketone component, wherein (i) said polyaryletherketone component has a surface and (ii) said surface has a wettability such that a contact angle of a bead of water positioned on said surface has a value less than 78°.

4. The prosthetic device of claim 3, wherein:

said contact angle is about 51°.

5. A polyaryletherketone component, comprising:

a surface having a wettability such that a contact angle of a bead of water positioned on said surface has a value less than 78°.

* * * * *